(12) United States Patent
Beck et al.

(10) Patent No.: US 12,251,324 B2
(45) Date of Patent: *Mar. 18, 2025

(54) REMOVABLE INCLINATION GUIDE FOR AN IMPLANT INSERTION TOOL AND ASSOCIATED SURGICAL METHOD

(71) Applicant: DEPUY IRELAND UNLIMITED COMPANY, Ringaskiddy (IE)

(72) Inventors: Clinton A. Beck, Fort Wayne, IN (US); Darron G. Peddle, Warsaw, IN (US); James A. Anderson, York (GB)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 0 days.

This patent is subject to a terminal disclaimer.

(21) Appl. No.: 18/112,208

(22) Filed: Feb. 21, 2023

(65) Prior Publication Data
US 2023/0190493 A1 Jun. 22, 2023

Related U.S. Application Data

(63) Continuation of application No. 16/702,833, filed on Dec. 4, 2019, now Pat. No. 11,583,417.

(51) Int. Cl.
*A61F 2/46* (2006.01)

(52) U.S. Cl.
CPC .... *A61F 2/4609* (2013.01); *A61F 2002/4629* (2013.01); *A61F 2002/4687* (2013.01)

(58) Field of Classification Search
CPC ............ A61F 2/4609; A61F 2002/4687; A61F 2002/4629; A61B 90/06; A61B 2090/067
See application file for complete search history.

(56) References Cited

U.S. PATENT DOCUMENTS

| | | |
|---|---|---|
| 3,367,337 A | 2/1968 | Javna et al. |
| 5,098,437 A | 3/1992 | Kashuba et al. |
| 5,284,483 A | 2/1994 | Johnson et al. |
| 5,364,403 A | 11/1994 | Petersen et al. |
| 5,752,954 A | 5/1998 | Mata et al. |
| 5,984,939 A | 11/1999 | Yoon |
| 7,241,074 B2 | 7/2007 | Thomke et al. |

(Continued)

FOREIGN PATENT DOCUMENTS

| | | |
|---|---|---|
| DE | 10202582 C1 | 9/2003 |
| DE | 102012104390 B4 | 10/2015 |

(Continued)

OTHER PUBLICATIONS

Smith & Nephew R3 Acetabular System, Poly Anteverted Liners Surgical Technique, 2023, 24 pages.

(Continued)

*Primary Examiner* — Anu Ramana
(74) *Attorney, Agent, or Firm* — Barnes & Thornburg LLP

(57) ABSTRACT

An inclination guide for use with an implant insertion tool during a surgical procedure includes a unitary body having a clip configured to be coupled to a mounting surface of the implant insertion tool, an elongated riser extending from the clip, and an elongated indicator extending from the elongated riser to a distal end. Such a design allows for an inexpensive and lightweight inclination guide that may be easily and quickly adjusted after assembly.

13 Claims, 11 Drawing Sheets

(56) References Cited

U.S. PATENT DOCUMENTS

| | | | |
|---|---|---|---|
| 7,294,133 B2* | 11/2007 | Zink | A61B 17/1778 606/96 |
| 7,780,673 B2 | 8/2010 | Acker et al. | |
| 8,230,863 B2* | 7/2012 | Ravikumar | A61B 90/50 403/56 |
| 8,403,869 B2* | 3/2013 | Kasasbeh | A61M 25/09041 600/585 |
| 8,603,180 B2 | 12/2013 | White et al. | |
| 8,834,480 B2 | 9/2014 | Hudak, Jr. et al. | |
| 9,055,975 B2 | 6/2015 | Satterthwaite | |
| 9,095,448 B2 | 8/2015 | Birkbeck et al. | |
| 9,295,566 B2 | 3/2016 | Birkbeck et al. | |
| 9,308,102 B2 | 4/2016 | McCarthy et al. | |
| 9,439,781 B2 | 9/2016 | Gibson | |
| 10,881,530 B2 | 1/2021 | Donaldson et al. | |
| 11,026,811 B2 | 6/2021 | Sherman et al. | |
| 2003/0105470 A1 | 6/2003 | White | |
| 2005/0107799 A1 | 5/2005 | Graf et al. | |
| 2007/0051002 A1 | 3/2007 | Sherry et al. | |
| 2007/0293869 A1 | 12/2007 | Conte et al. | |
| 2010/0121335 A1 | 5/2010 | Penenberg et al. | |
| 2010/0183814 A1* | 7/2010 | Rios | A63B 60/00 427/387 |
| 2011/0184419 A1 | 1/2011 | Meridew et al. | |
| 2011/0224674 A1 | 9/2011 | White et al. | |
| 2012/0116410 A1* | 5/2012 | Kortenbach | A61B 17/17 606/96 |
| 2012/0226283 A1 | 9/2012 | Nairus et al. | |
| 2014/0052137 A1 | 2/2014 | Gibson et al. | |
| 2014/0094925 A1 | 4/2014 | Satterthwaite | |
| 2014/0137352 A1* | 5/2014 | Golla | B25G 1/02 15/160 |
| 2016/0184109 A1 | 6/2016 | Davenport et al. | |
| 2016/0220385 A1 | 8/2016 | Falardeau et al. | |
| 2018/0296365 A1 | 10/2018 | Nielsen et al. | |
| 2019/0231446 A1 | 8/2019 | Bowling et al. | |
| 2021/0169661 A1 | 6/2021 | Beck et al. | |

FOREIGN PATENT DOCUMENTS

| | | |
|---|---|---|
| JP | 2013528420 A | 7/2013 |
| JP | 2014519893 A | 8/2014 |

OTHER PUBLICATIONS

Zimmer Biomet, G7 Acetabular System Surgical Technique, 2019, 48 pages.
Zimmer Biomet, Continuum Acetabular System Surgical System, 2018, 28 pages.
International Search Report for International Application No. PCT/EP2020/084686, Mar. 3, 2021, 2 pages.
Notice of Reasons for Refusal drafted Jul. 12, 2024 in co-pending JP application 2022-533516.

* cited by examiner

REMOVABLE INCLINATION GUIDE FOR AN IMPLANT INSERTION TOOL AND ASSOCIATED SURGICAL METHOD

CROSS-REFERENCE TO RELATED APPLICATION

The present application is a continuation of U.S. application Ser. No. 16/702,833, entitled "REMOVABLE INCLINATION GUIDE FOR AN IMPLANT INSERTION TOOL AND ASSOCIATED SURGICAL METHOD," which was filed on Dec. 4, 2019, and which issued as U.S. Pat. No. 11,583,417 on Feb. 21, 2023, which is incorporated herein by reference in its entirety.

TECHNICAL FIELD

The present disclosure relates generally to orthopaedic surgical instruments and, more particularly, to surgical instruments used to trial and install an acetabular cup component.

BACKGROUND

Joint arthroplasty is a well-known surgical procedure by which a diseased and/or damaged natural joint is replaced by a prosthetic joint. For example, in a hip arthroplasty surgical procedure, a patient's natural hip ball and socket joint is partially or totally replaced by a prosthetic hip joint. A typical prosthetic hip joint includes an acetabular cup component and a femoral head component. An acetabular cup component generally includes an outer shell configured to engage the acetabulum of the patient and an inner bearing or liner coupled to the shell and configured to engage the femoral head. The femoral head component and inner liner of the acetabular component form a ball and socket joint that approximates the natural hip joint.

To facilitate the replacement of the natural joint with a prosthetic hip joint, orthopaedic surgeons may use a variety of orthopaedic surgical instruments such as, for example, reamers, drill guides, drills, positioners, insertion tools and/or other surgical instruments. The acetabular component is typically inserted into the patient's acetabulum using an acetabular prosthetic component inserter. Poor alignment of the acetabular prosthetic component relative to the patient's bony anatomy can result in component loosening and/or dislocation over time and use of the prosthetic hip joint.

SUMMARY

According to one aspect, an inclination guide for use with an implant insertion tool during a surgical procedure includes a unitary body having a clip configured to be coupled to a mounting surface of the implant insertion tool, an elongated riser extending from the clip to a first joint, and an elongated indicator extending from the first joint of the elongated riser to a distal end. The clip defines an interior volume and an imaginary tool axis that extends through the interior volume. The elongated riser extends from the clip away from the imaginary tool axis to the first end. The elongated indicator and the imaginary tool axis define an indication angle.

In an embodiment, the unitary body is a molded polymeric body. The unitary body may be formed from polyphenylsulfone (PPSU). In another embodiment, the unitary body may be formed from a metallic material.

In an embodiment, the clip includes a first curved arm that extends away from the elongated riser to a first end and a second curved arm that extends away from the elongated riser to a second end. The first curved arm and the second curved arm cooperate to define the interior volume. The first end and the second end cooperate to define a slot that provides access to the interior volume.

In an embodiment, a first rounded ledge is included on the first end of the first curved arm and a second rounded ledge is included on the second end of the second curved arm. Each of the first rounded ledge and the second rounded ledge curves away from the slot.

In an embodiment, wherein each of the first end of the first curved arm and the second end of the second curved arm have a chamfered edge. The chamfered edges are configured to engage the implant insertion tool and to urge the slot open when engaged with the implant insertion tool.

In an embodiment, the the first curved arm and the second curved arm may define a plano-concave interior surface configured to engage a cylindrical mounting surface of the implant insertion tool. In another embodiment, the first curved arm and the second curved arm may define a tapered concave interior surface configured to engage a conical frustum mounting surface of the implant insertion tool.

In an embodiment, the clip includes interior surface that confronts the mounting surface of the implant insertion tool while the clip is coupled to the mounting surface. The interior surface includes three contact points, and each of the three contact points is configured to engage the mounting surface of the implant insertion tool.

In an embodiment, the clip includes a first tooth and a second tooth that extend inwardly into the interior volume from an interior surface of the clip toward the imaginary tool axis. The first tooth and the second tooth are configured to engage a respective groove of the mounting surface. The mounting surface may include a plurality of ridges parallel to the imaginary tool axis. Each pair of ridges is separated by a groove.

In an embodiment, the clip includes a first curved arm that extends away from the elongated riser to a first end and a second curved arm that extends away from the elongated riser to a second end. The first curved arm and the second curved arm cooperate to define the interior volume. The first end and the second end cooperate to define a slot that provides access to the interior volume. The first tooth is on the first end of the first curved arm, and the second tooth is on the second end of the second curved arm.

According to another aspect, a method of performing an orthopaedic surgical procedure on a surgically-prepared acetabulum of a patient's hip includes attaching an inclination guide, that is separate from an implant insertion tool, to the implant insertion tool by passing a portion of the implant insertion tool through a slot in a clip of the inclination guide, inserting a distal end of the implant insertion tool into the surgically-prepared acetabulum of the patient's hip in response to attaching the inclination guide, and measuring an inclination angle of the implant insertion tool using an elongated indicator of the inclination guide while the distal end of the implant insertion tool is inserted into the surgically prepared acetabulum.

In an embodiment, the method may further include rotating the inclination guide about a tool axis defined by a body of the implant insertion tool subsequent to attaching the inclination guide. Measuring the inclination angle may be performed subsequent to rotating the inclination guide.

In an embodiment, attaching the inclination guide includes engaging a tooth of the clip with a first groove of a mounting surface of the implant insertion tool, and rotating the inclination guide includes moving the tooth of the clip from the first groove to a second groove of the mounting surface. The mounting surface includes a plurality of ridges parallel to the tool axis, and each pair of ridges is separated by a groove.

In another embodiment, the method further includes sliding the inclination guide in a direction along a tool axis of the implant insertion tool subsequent to attaching the inclination guide, such that an interior surface of the clip is engaged with a conical frustum mounting surface of the implant insertion tool.

In an embodiment, attaching the inclination guide includes pressing on a pair of rounded ledges on each end of the clip.

In an embodiment, the method further includes removing the inclination guide by passing the portion of the implant insertion tool out through the slot in the clip subsequent to measuring the inclination angle. Removing the inclination guide may include pulling on a pair of rounded ledges on each end of the clip.

BRIEF DESCRIPTION OF THE DRAWINGS

The detailed description particularly refers to the following figures, in which.

DETAILED DESCRIPTION OF THE DRAWINGS

Figure 1:
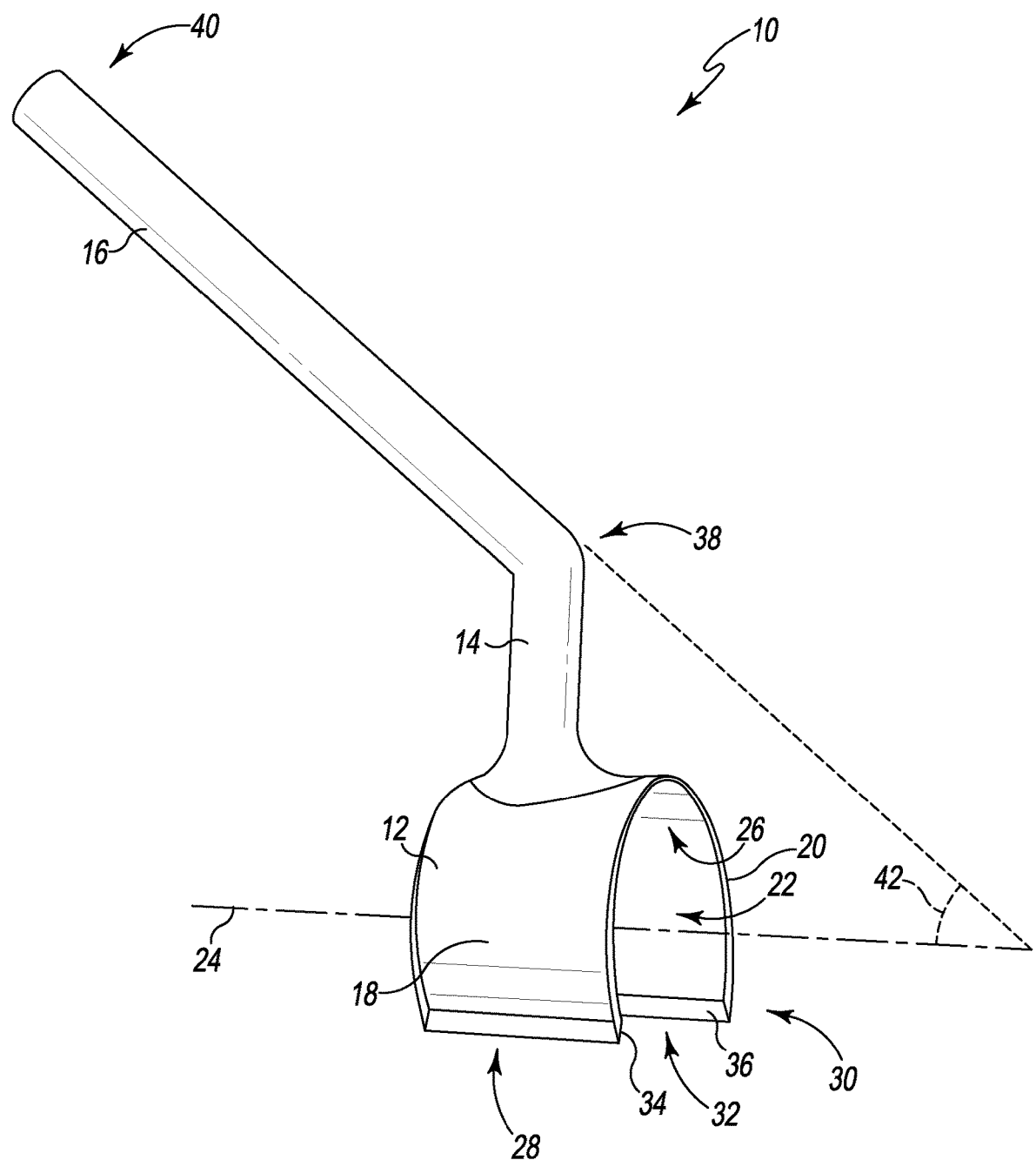
FIG. 1 is a perspective view of an alignment guide for use with an implant insertion tool.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention.

Terms representing anatomical references, such as anterior, posterior, medial, lateral, superior, inferior, etcetera, may be used throughout this disclosure in reference to both the orthopaedic implants described herein and a patient's natural anatomy. Such terms have well-understood meanings in both the study of anatomy and the field of orthopaedics. Use of such anatomical reference terms in the specification and claims is intended to be consistent with their well-understood meanings unless noted otherwise.

Referring now to FIGS. 1-5, there is shown an alignment guide 10 for use with an implant insertion tool 44 for inserting an acetabular cup component into the acetabulum of a patient during an orthopaedic surgical procedure. As will be described in more detail below, the alignment guide 10 is configured to be assembled with the implant insertion tool 44, and the radial angle of the alignment guide 10 may be adjusted after assembly as desired by the orthopaedic surgeon or caregiver. As described further below, the alignment guide 10 may be used with a variety of different types of insertion tools, including straight and curved implant insertion tools. Accordingly, the alignment guide 10 may improve ease of use and reduce operation time while being adaptable to surgeon preference. Additionally, in some embodiments, the alignment guide 10 may be constructed from lightweight materials at low cost. It should be appreciated that although the concepts of the present disclosure are herein described in regard to an implant insertion tool for use in an orthopaedic hip procedure, the concepts of the present disclosure may be utilized in the design of other types of alignment guides, in particular for other procedures where transverse alignment is required.

The illustrative alignment guide 10 has a unitary body formed from a single piece of molded polymer. For example, the alignment guide 10 may be formed from a sulfone polymer such as polyphenylsulfone (PPSU). Additionally or alternatively, in some embodiments, the alignment guide 10 may be formed from any resilient polymeric material. Alternatively, in other embodiments, the alignment guide 10 may be formed from metallic material.

The alignment guide 10 includes a clip 12, a riser 14, and an elongated indicator 16. The clip 12 includes a pair of curved arms 18, 20 that define an interior volume 22, as well as an imaginary axis 24 that extends through the interior volume 22. The arms 18, 20 include an interior surface 26 that extends from a distal end 28 of the arm 18 to a distal end 30 of the arm 20. The ends 28, 30 define a slot 32 therebetween through which the interior volume 22 is accessible.

Figure 2:
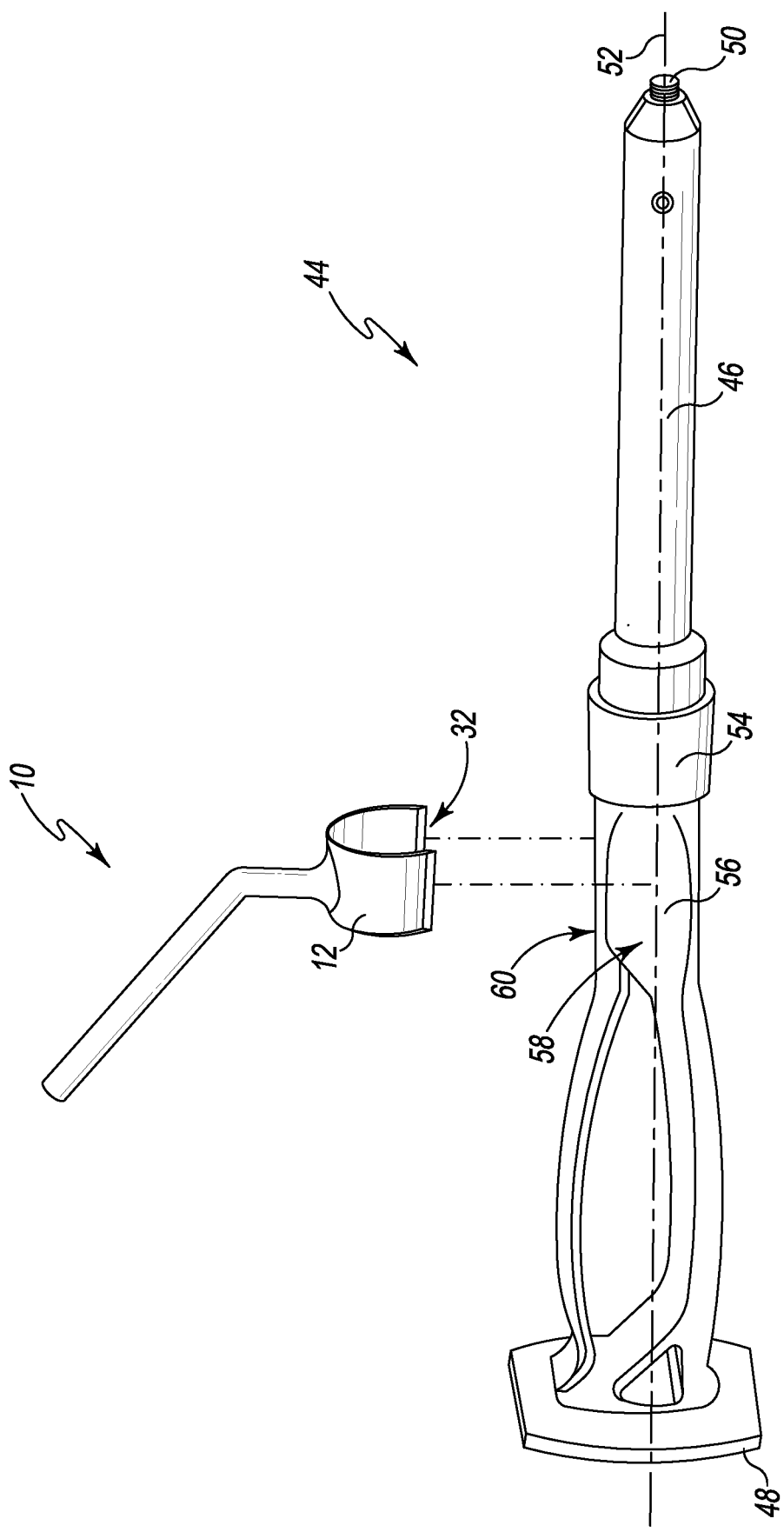
FIG. 2 is a side view of the alignment guide of FIG. 1 and an implant insertion tool showing the alignment guide positioned near the implant insertion tool and in the process of being attached to the implant insertion tool.
Figure 3:
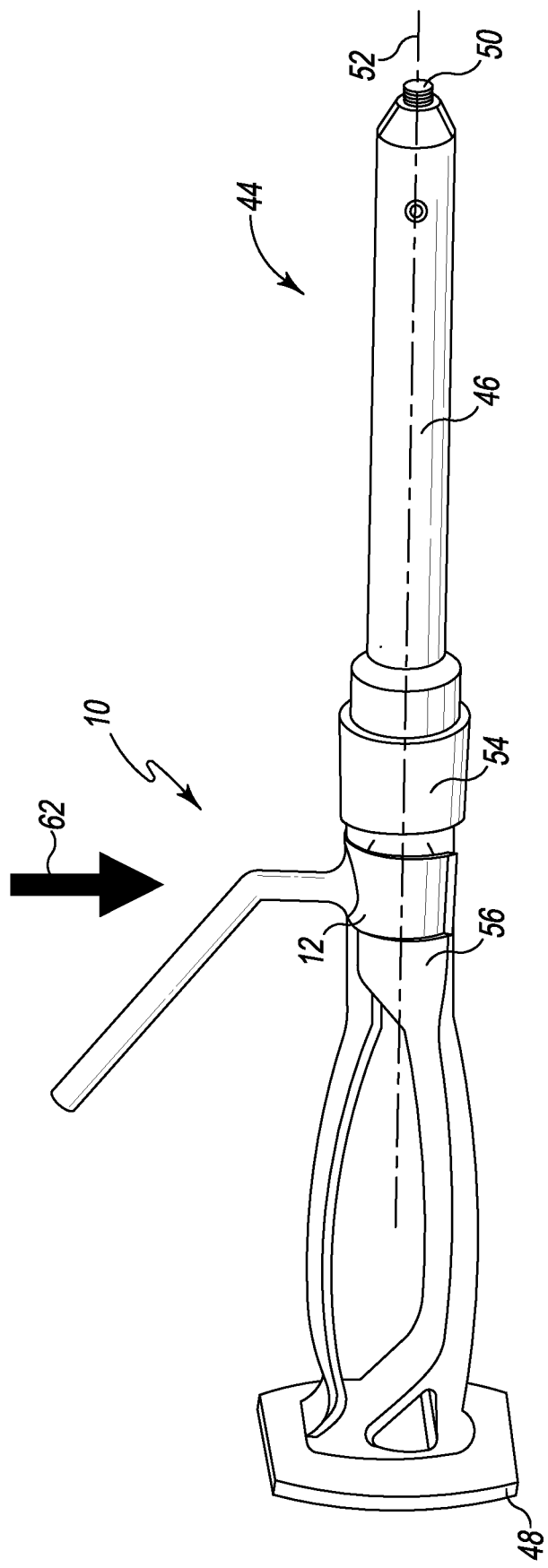
FIG. 3 is a side view of the alignment guide and the implant insertion tool of FIGS. 1-2 showing the alignment guide clipped or attached to the implant insertion tool.

As described further below, when the alignment guide 10 is coupled to the implant insertion tool 44, a portion of the implant insertion tool 44 passes through the slot 32 into the interior volume 22, and the interior surface 26 of the arms 18, 20 contacts or engages a corresponding mounting surface of the implant insertion tool 44. Each end 28, 30 of the corresponding arms 18, 20 includes a corresponding chamfered edge 34, 36. Because the slot 32 is undersized relative to the body of the insertion tool 44, the arms 18, 20 are urged apart when the chamfered edges 34, 36 engage the body of the implant insertion tool 44, which increases the width of the slot 32 and allows the implant insertion tool 44 to pass into the interior volume 22 as shown in FIGS. 2 and 3.

The riser 14 of the alignment guide 10 extends away from the clip 12 perpendicular to the axis 24 toward a dogleg joint 38. Although the illustrative riser 14 is embodied as a post extending perpendicular from the clip 12, it should be understood that the riser 14 may have another shape and/or extend at another angle away from the axis 24 in other embodiments. Additionally, in some embodiments, the riser 14 may be adapted to provide a gripping surface for a surgeon, for example by including mounds, knurling, or other grip-enhancing features.

The indicator 16 extends from the dogleg joint 38 of the riser 14 to a distal end 40. The illustrative indicator 16 is embodied as a post; however, similar to the riser 14, in other embodiments the indicator 16 may be otherwise shaped. The indicator 16 and the axis 24 define an indication angle 42. The illustrative indication angle 42 is defined as 35 degrees; however, in other embodiments the indication angle 42 may be 40 degrees or another angle. In some embodiments, the magnitude of the indication angle 42 may be molded into the clip 12 or otherwise indicated visually on the alignment guide 10 via a label or text. As described further below, a surgeon may use the indicator 16 to visually measure and confirm the inclination angle of the acetabular cup as it is installed in the patient's hip. The surgeon may select among multiple alignment guides 10 based on the desired indication angle 42.

The particular indication angle 42 may be selected based upon the desired surgical approach, the desired final inclination angle of the acetabular cup, the alignment of the patient's hip in relation to the operating table, and/or other factors. For example, in some embodiments, the angle of the patient's hip, the desired final inclination angle of the acetabular cup, and the indication angle 42 may sum to 90 degrees (i.e., vertical in relation to the operating room). As an example, for a posterior surgical approach, the patient alignment angle may be 10 degrees, the desired final inclination angle of the acetabular cup may be 45 degrees, and the indication angle 42 may be 35 degrees such that the indicator 16 is substantially vertical relative to the operating room when the acetabular cup is properly aligned to 45 degrees. As another example, for an anterior surgical approach, the patient alignment angle may be five degrees, the desired final inclination angle of the acetabular cup may be 45 degrees, and the indication angle 42 may be 40 degrees. Of course, other angles may be used.

Referring now to FIGS. 2-5, in use, the alignment guide 10 may be attached to the implant insertion tool 44 as discussed above. The illustrative implant insertion tool 44 has an elongated metallic body 46 having an impact head 48 on its proximal end and an attachment mechanism 50 on its distal end. The body 46 defines an imaginary tool axis 52 that extends from the attachment mechanism 50 to the impact head 48. The implant insertion tool 44 may have a straight body 46 or, similar to the tool shown in FIGS. 10-12, in some embodiments the body 46 may be curved, for example to avoid patient anatomy.

The impact head 48 of the implant insertion tool 44 is illustratively embodied as a metallic strike plate formed in the body 46. However, it should be appreciated that the strike plate could be embodied as a separate component welded or otherwise secured to the body 46. In use, the surgeon holds the assembled implant insertion tool 44 via the body 46 and strikes impact head 48 with a surgical mallet, sledge, or other impaction tool to drive an acetabular cup component 70 into the patient's surgically-prepared acetabular surface 74 (see FIG. 13).

The body 46 includes a mounting surface 54 formed on part of the body 46. The illustrative mounting surface 54 is embodied as a conic frustum; however, in other embodiments the mounting surface 54 may be cylindrical or have another shape. The body 46 further includes an attachment section 56 adjacent to the mounting surface 54. In the illustrative embodiment, the attachment section 56 is narrower than the mounting surface 54 in at least one dimension. For example, the illustrative attachment part 56 includes flat sides 58, 60, which oppose each other to reduce the width of the attachment section 56.

Figure 13:
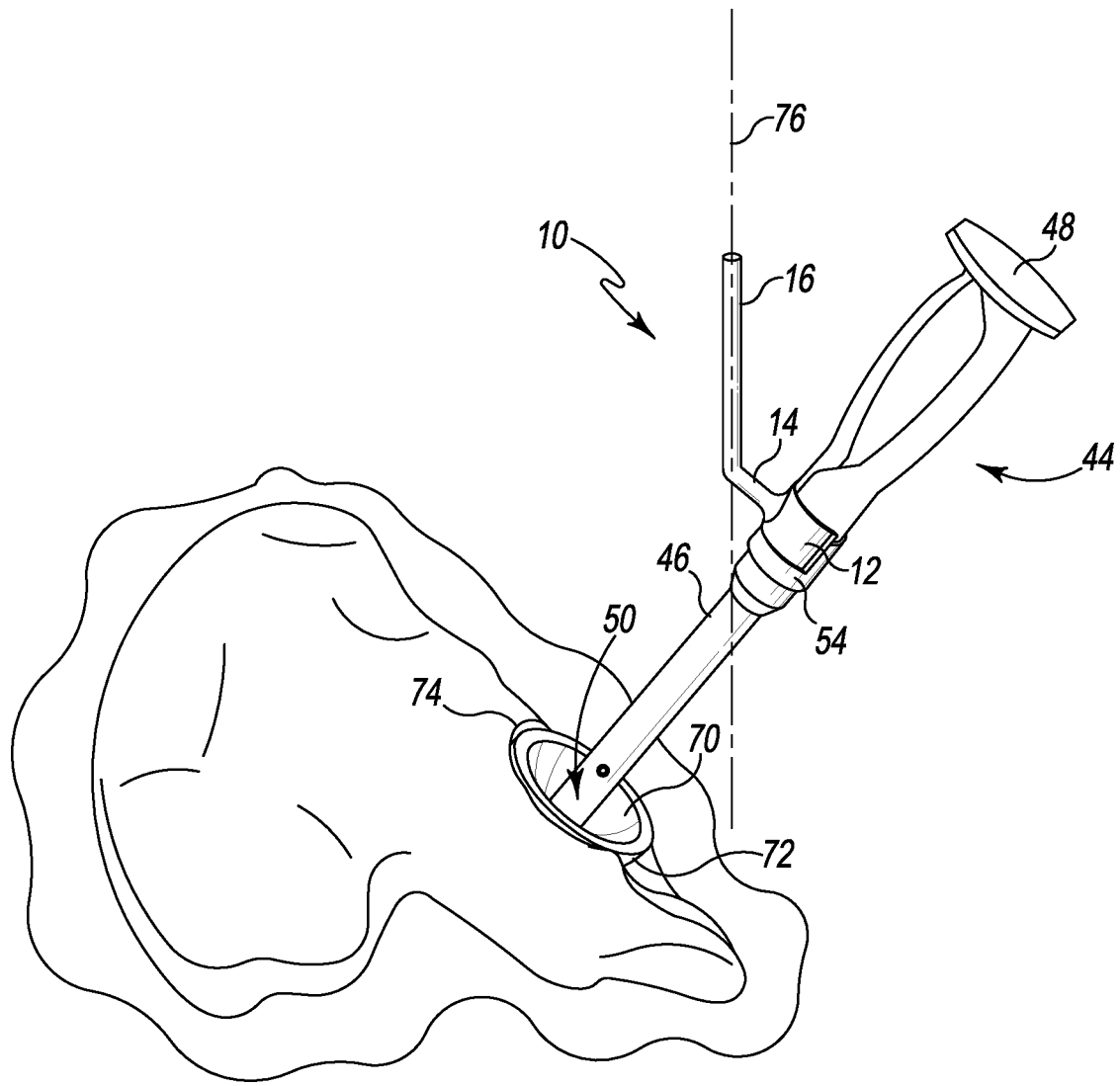
FIG. 13 is a perspective view showing an acetabular cup component being installed in the acetabulum of a patient's hip by use of an alignment guide and an implant insertion tool of FIGS. 1-12.

In use, the alignment guide 10 may be utilized by a surgeon with an implant insertion tool 44 to implant the acetabular cup component 70 into a surgically-prepared acetabulum 84 of a patient (see FIG. 13). As shown in FIG. 3, the alignment guide 10 may be coupled, attached, or otherwise clipped to the implant insertion tool 44 at the attachment section 56. To do so, the surgeon or other user places the clip 12 of the alignment guide 10 in contact with the attachment section 56 and then presses the alignment guide 10 in a downwardly direction 62 toward the implant insertion tool 44. Illustratively, as the alignment guide 10 contacts the implant insertion tool 44, the chamfered edges 34, 36 engage with the flat sides 58, 60 of the attachment part 56 and force the slot 32 open to allow the attachment section 56 into the interior volume 22. The surgeon may slide the alignment guide 10 onto the implant insertion tool 44 in the direction 62 until the interior surface 26 contacts the implant insertion tool 44. After contacting the implant insertion tool 44, the clip 12 surrounds the tool axis 52.

Figure 4:
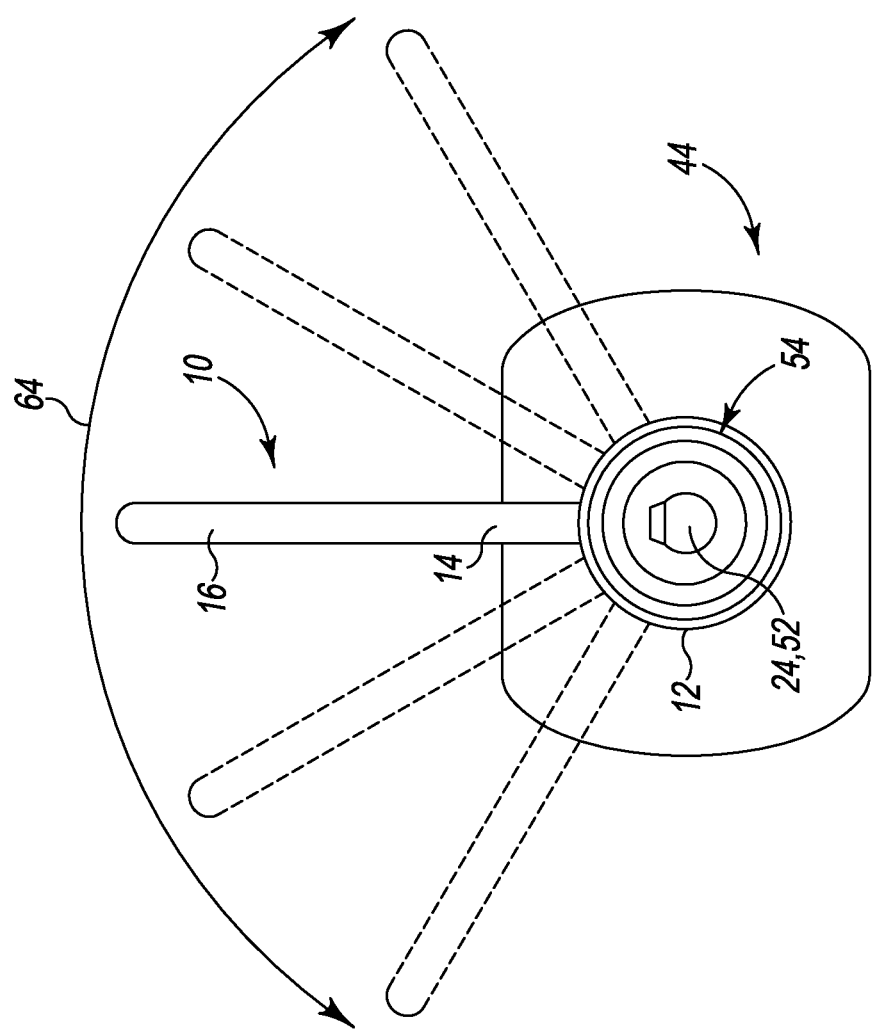
FIG. 4 is a rear view of the alignment guide and implant insertion tool of FIGS. 1-3 showing the alignment guide being rotated about the axis of the implant insertion tool.

In some embodiments, as shown in FIG. 4, the surgeon or other user may rotate the alignment guide 10 about the tool axis 52. Because the mounting surface 54 and the interior surface 26 are relatively smooth, the alignment guide 10 may be freely rotated to any angle 64 about the tool axis 52. The surgeon may select the angle based on individual preference, to adjust to patient anatomy, or for other reasons.

Figure 5:
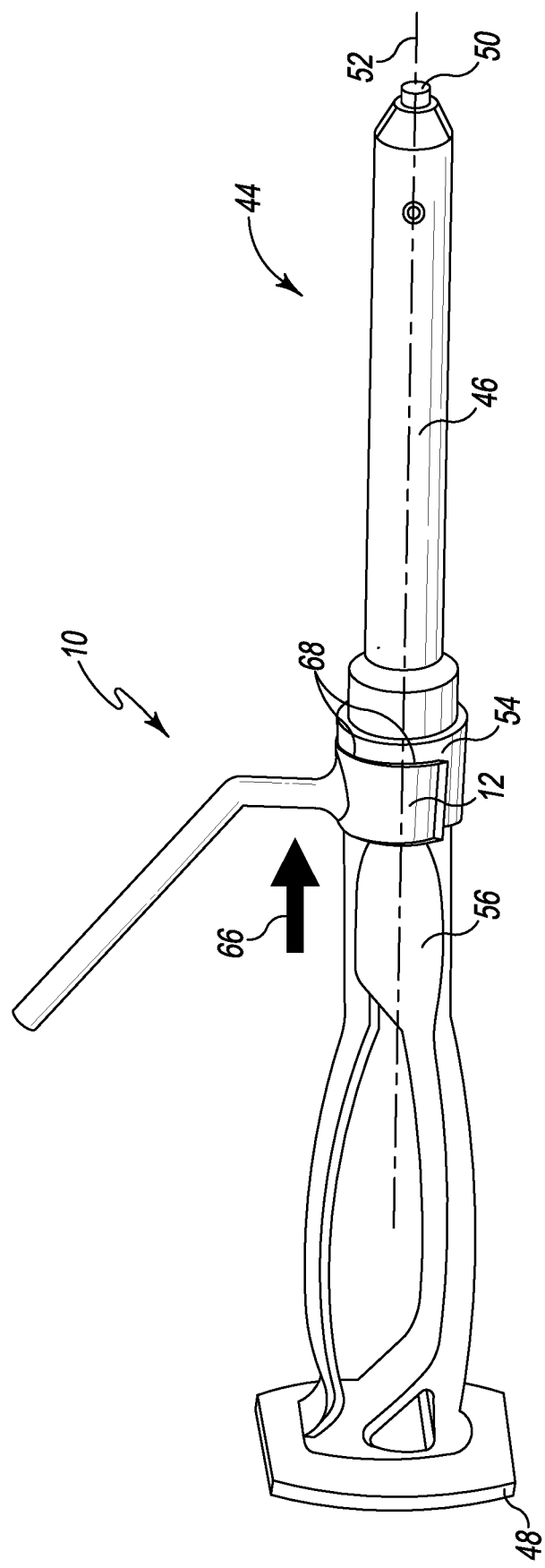
FIG. 5 is a side view of the alignment guide and implant insertion tool of FIGS. 1-4 showing the alignment guide locked on the implant insertion tool.

As shown in FIG. 5, after selecting the appropriate rotational angle, the surgeon or other user presses or slides the alignment guide 10 in a direction 66 toward the mounting surface 54. As the alignment guide 10 moves onto the mounting surface 54, the tapered interior surface 26 of the alignment guide 10 engages against the conical frustum mounting surface 54 of the implant insertion tool 44. In the illustrative embodiment, the interior surface 26 is formed so as to contact the mounting surface 54 at three contact points 68 of the interior surface 26. The contact points 68 may be formed, for example, via mounds, tabs, ridges, or other features that protrude from the interior surface 26. Of course, in other embodiments, additional contact points 68 may be used.

When engaged, the alignment guide 10 establishes a friction lock in position on the mounting surface 54. After being locked in position, the alignment guide 10 remains at the rotational angle 64 selected by the surgeon due to frictional forces between the alignment guide 10 and the implant insertion tool 44. The surgeon may unlock the alignment guide 10 by moving the alignment guide 10 in a direction opposite the direction 66, which allows the surgeon to adjust the rotational angle of the alignment guide 10. Although illustrated as establishing a taper fit in FIGS. 2-5, it should be understood that in other embodiments, the alignment guide 10 may clip onto the implant insertion tool 44 using any suitable interference fit. For example, illustrative embodiments of alignment guides 10 that attach to the implant insertion tool 44 using an interference fit are shown below in connection with FIGS. 6-12.

Figure 6:
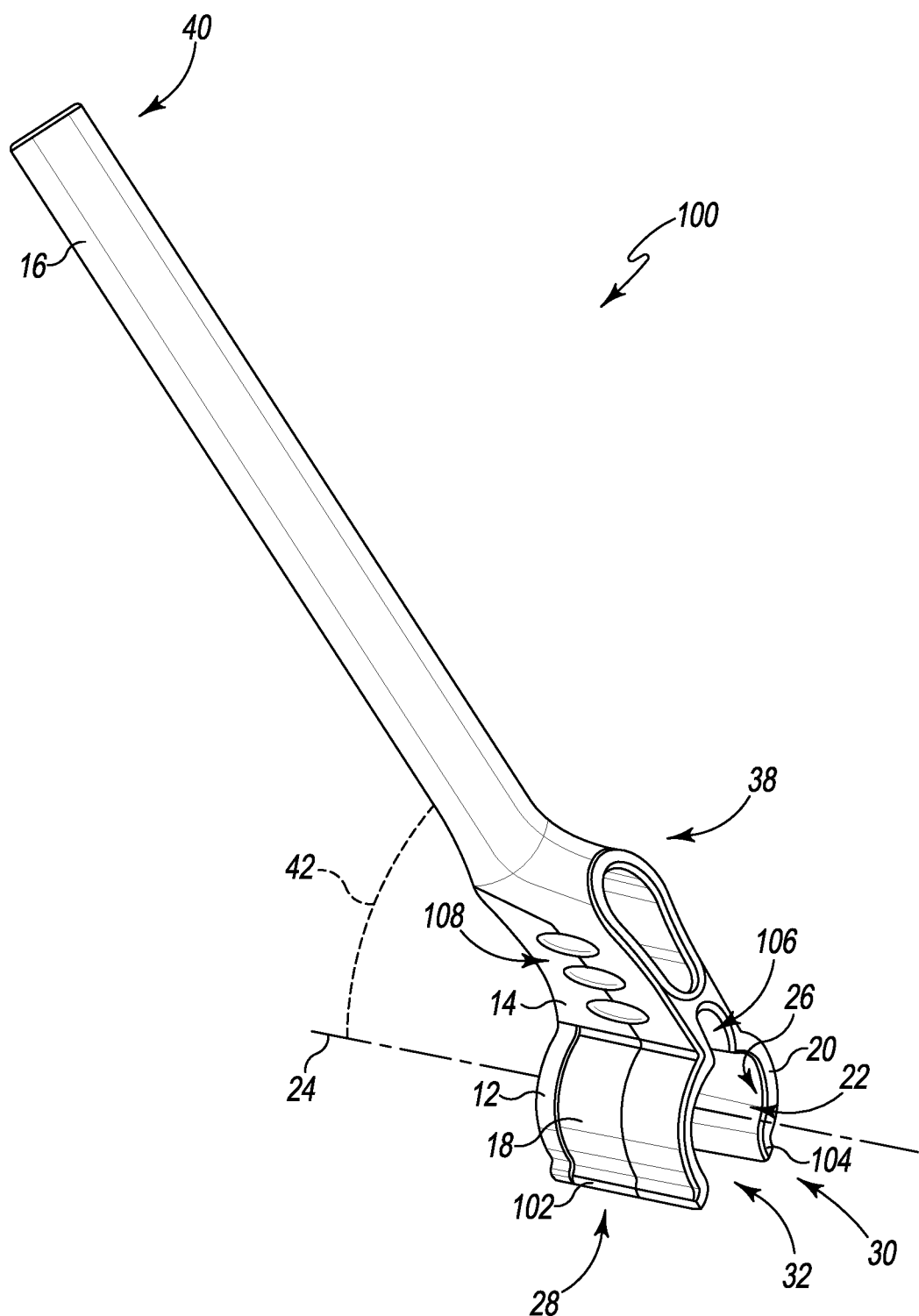
FIG. 6 is a perspective view of another illustrative embodiment of an alignment guide for use with an implant insertion tool.
Figure 7:
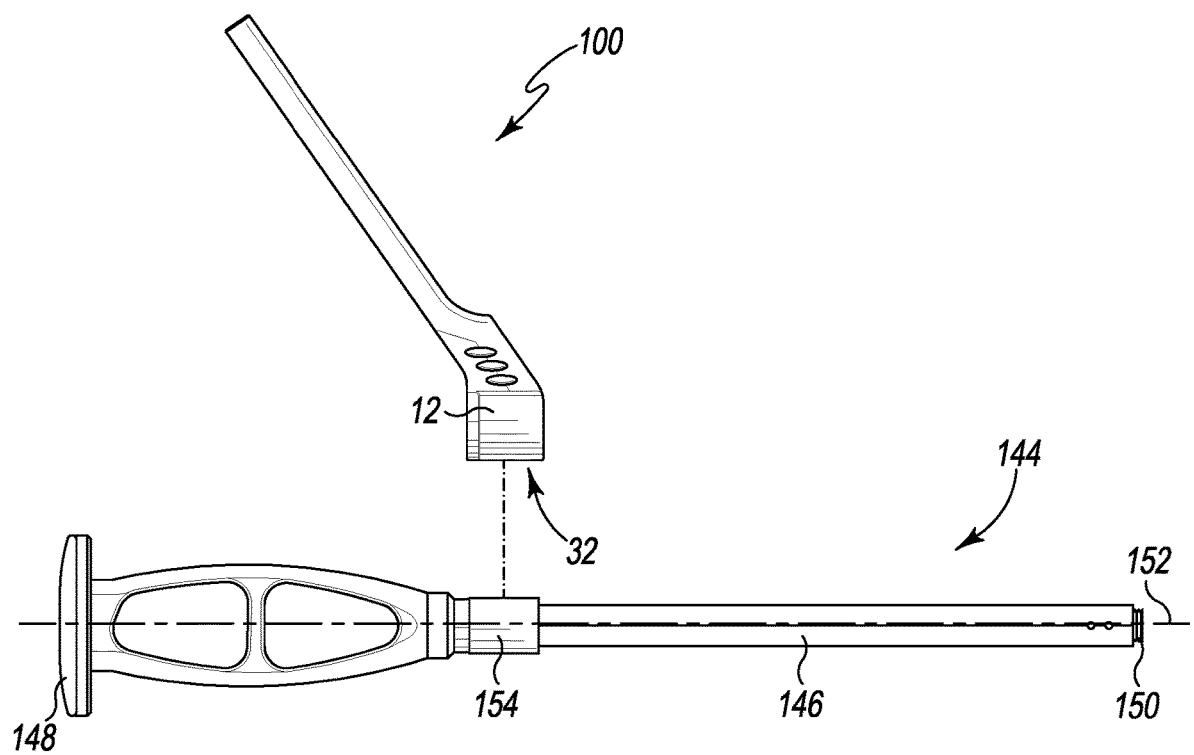
FIG. 7 is a side view of the alignment guide of FIG. 6 and an implant insertion tool showing the alignment guide positioned near the implant insertion tool and in the process of being attached to the implant insertion tool.
Figure 8:
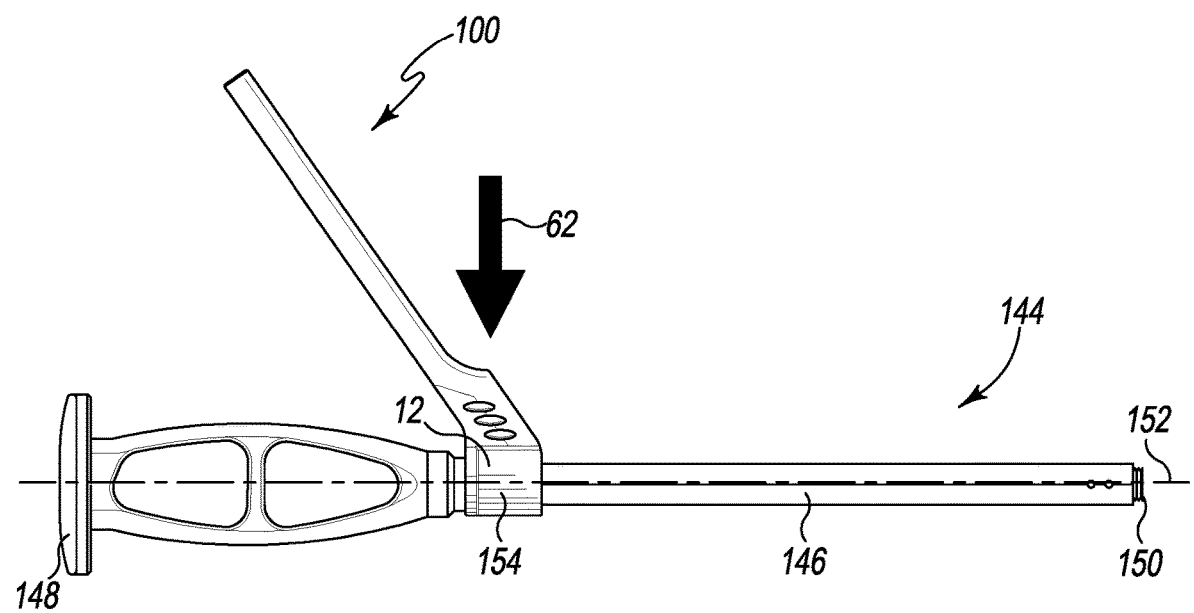
FIG. 8 is a side view of the alignment guide and implant insertion tool of FIGS. 6-7 showing the alignment guide locked on the implant insertion tool.
Figure 9:
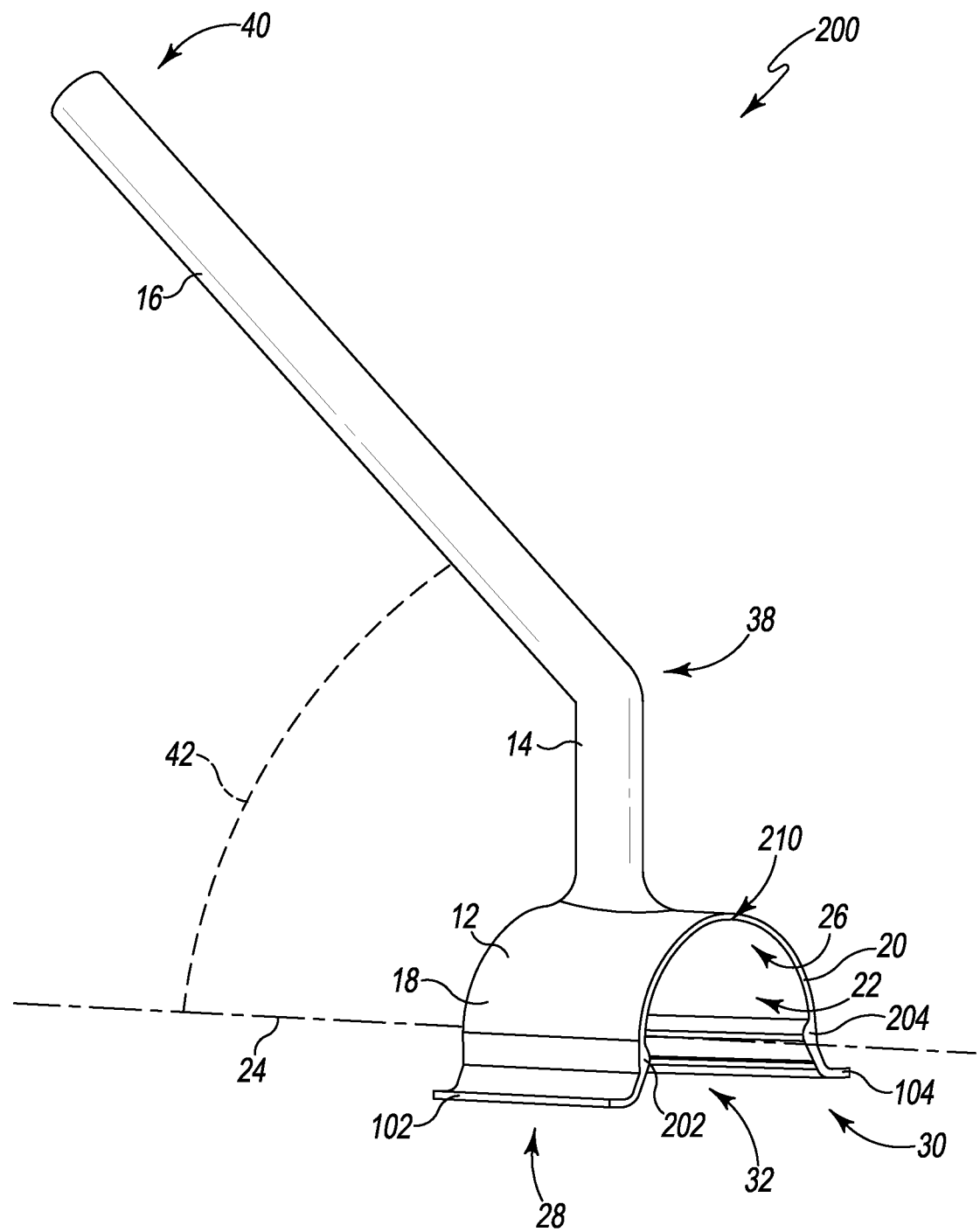
FIG. 9 is a perspective view of another illustrative embodiment of an alignment guide for an implant insertion tool.

Referring now to FIGS. 6-8, there is shown an alignment guide 100 for use with an implant insertion tool for inserting an acetabular cup component into the acetabulum of a patient during an orthopaedic surgical procedure. Similar to the alignment guide 10, the illustrative alignment guide 100 has a unitary body formed from a single piece of molded polymer. For example, the alignment guide 100 may be formed from a sulfone polymer such as polyphenylsulfone (PPSU). Additionally or alternatively, in some embodiments, the alignment guide 100 may be formed from any resilient polymeric material. Alternatively, in other embodiments, the alignment guide 100 may be formed from metallic material.

Also similar to the alignment guide 10, the alignment guide 100 includes a clip 12, a riser 14, and an elongated indicator 16. The clip 12 includes a pair of curved arms 18, 20 that define an interior volume 22, as well as an imaginary axis 24 that extends through the interior volume 22. The arms 18, 20 include an interior surface 26 that extends from a distal end 28 of the arm 18 to a distal end 30 of the arm 20. The ends 28, 30 define a slot 32 therebetween which the interior volume 22 is accessible. The interior surface 26 forms a plano-concave curve that engages a cylindrical mounting surface 154 of an insertion tool 144, as described further below.

As described further below, when the alignment guide 100 is coupled to the implant insertion tool 144, the mounting surface 154 of the implant insertion tool 144 passes through the slot 32 into the interior volume 22, and the interior surface 26 of the arms 18, 20 contacts or engages the mounting surface 154. The illustrative arms 18, 20 further include rounded ledges 102, 104 on the respective ends 28, 30. The ledges 102, 104 curve away from the slot 32 and may allow for ease of attachment or removal of the alignment guide 100 similar to the chamfered edges 34, 36 of the alignment guide 10. For example, the arms 18, 20 are urged apart when the rounded ledges 102, 104 engage the body of the implant insertion tool 144, which increases the width of the slot 32 and allows the implant insertion tool 144 to pass into the interior volume 22 as shown in FIGS. 7 and 8. Additionally, a surgeon may press or pull on the ledges 102, 104 to ease attaching or removing the alignment guide 100, respectively. The illustrative clip 12 includes a relief opening 106 between the arms 18, 20 that allows the arms 18, 20 to separate.

The riser 14 of the alignment guide 100 extends away from the clip 12 and the axis 24 toward a dogleg joint 38. The illustrative riser 14 includes a grouping of mounds or ridges 108 formed in the surface of the riser 14 to provide a gripping surface for a surgeon. The illustrative riser 14 is formed to be hollow. However, it should be understood that in other embodiments the riser 14 may be solid or otherwise shaped. For example, in some embodiments, the riser 14 may be embodied as a rod extending from the clip 12 to the dogleg joint 38, similar to the riser 14 of the alignment guide 10.

The indicator 16 extends from the dogleg joint 38 of the riser 14 to a distal end 40. The illustrative indicator 16 is formed to be hollow; however, similar to the riser 14, in other embodiments the indicator 16 may be solid or otherwise shaped. The indicator 16 and the axis 24 define an indication angle 42. The illustrative indication angle 42 is defined as 35 degrees; however, in other embodiments the indication angle 42 may be 40 degrees or another angle. In some embodiments, the magnitude of the indication angle 42 may be molded into the clip 12 or otherwise indicated visually on the alignment guide 100 via a label or text. As described further below, a surgeon may use the indicator 16 to visually measure and confirm the inclination angle of the acetabular cup as it is installed in the patient's hip. The surgeon may select among multiple alignment guides 10 based on the desired indication angle 42. The surgeon may select the particular indication angle 42 as described above in connection with the alignment guide 10.

Referring now to FIGS. 7-8, in use, the alignment guide 100 may be attached to the implant insertion tool 144 as discussed above. Similar to the implant insertion tool of FIGS. 2-5, the illustrative implant insertion tool 144 has an elongated metallic body 146 having an impact head 148 on its proximal end and an attachment mechanism 150 on its distal end. The body 146 defines an imaginary tool axis 152 that extends from the attachment mechanism 150 to the impact head 148. The implant insertion tool 144 may have a straight body 146 or, similar to the tool shown in FIGS. 10-12, in some embodiments the body 146 may be curved, for example to avoid patient anatomy. The body 146 includes a mounting surface 154 formed on a section of the body 146. The illustrative mounting surface 154 is cylindrical.

The impact head 148 of the implant insertion tool 144 is illustratively embodied as a metallic strike plate formed in the body 146. However, it should be appreciated that the strike plate could be embodied as a separate component welded or otherwise secured to the body 146. In use, the surgeon holds the assembled implant insertion tool 144 via the body 146 and strikes impact head 148 with a surgical mallet, sledge, or other impaction tool to drive an acetabular cup component 70 into the patient's surgically-prepared acetabular surface 74 (see FIG. 13).

In use, the alignment guide 100 may be utilized by a surgeon with an implant insertion tool 144 to implant the acetabular cup component 70 into the surgically-prepared acetabulum 84 of a patient (see FIG. 13). As shown in FIG. 8, the alignment guide 100 may be coupled, attached, or otherwise clipped to the implant insertion tool 144 at the mounting surface 154. To do so, the surgeon or other user places the clip 12 of the alignment guide 100 in contact with the mounting surface 154 and then presses the alignment guide 100 in the downwardly direction 62 toward the implant insertion tool 144. Illustratively, as the alignment guide 100 contacts the implant insertion tool 144, the rounded ledges 102, 104 engage with the cylindrical mounting surface 154 and force the slot 32 open to allow the mounting surface 154 into the interior volume 22. The surgeon may slide the alignment guide 100 onto the implant insertion tool 144 in the direction 62 until the interior surface 26 contacts the implant insertion tool 144. After the interior surface 26 contacts the implant insertion tool 144, the clip 12 surrounds the tool axis 152. When attached to the mounting surface 154, the alignment guide 100 establishes an interference lock in position on the mounting surface 154.

Similar to the alignment guide 10 shown in FIG. 4, after attaching the alignment guide 100 to the implant insertion tool 144, in some embodiments the surgeon may rotate the alignment guide 100 about the tool axis 152. Because the mounting surface 154 and the interior surface 26 are relatively smooth, the alignment guide 100 may be freely rotated to any angle 64 about the tool axis 52. The surgeon may select the angle based on individual preference, to adjust to patient anatomy, or for other reasons. Additionally or alternatively, in some embodiments the surgeon may remove the alignment guide 100, reposition the alignment guide 100 at the desired angle 64 about the tool axis 52, and then re-attach the alignment guide 100 at the desired angle 64 as discussed above.

Referring now to FIGS. 9-12, another embodiment of an alignment guide 200 for use with an implant insertion tool for inserting an acetabular cup component into the acetabulum of a patient during an orthopaedic surgical procedure is shown. Similar to the alignment guides 10, 100, the illustrative alignment guide 200 has a unitary body formed from a single piece of molded polymer. For example, the alignment guide 200 may be formed from a sulfone polymer such as polyphenylsulfone (PPSU). Additionally or alternatively, in some embodiments, the alignment guide 200 may be formed from any resilient polymeric material. Alternatively, in other embodiments, the alignment guide 200 may be formed from metallic material.

Also similar to the alignment guides 10, 100, the illustrative alignment guide 200 includes a clip 12, a riser 14, and an elongated indicator 16. The clip 12 includes a pair of curved arms 18, 20 that define an interior volume 22, as well as an imaginary axis 24 that extends through the interior volume 22. The arms 18, 20 include an interior surface 26 that extends from a distal end 28 of the arm 18 to a distal end 30 of the arm 20. The ends 28, 30 define a slot 32 therebetween which the interior volume 22 is accessible. The interior surface 26 includes a pair of teeth or other projections 202, 204 that project into the interior volume 22. Each tooth 202, 204 is positioned at a respective end 28, 30 of the corresponding arm 18, 20.

Figure 10:
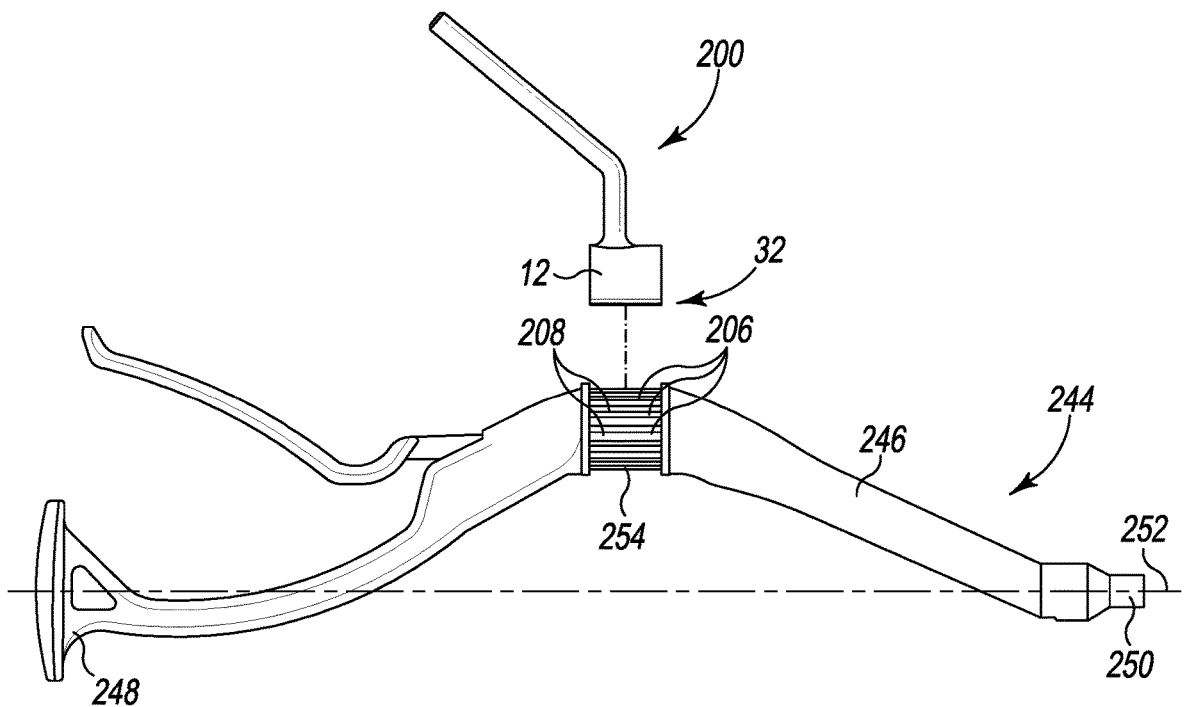
FIG. 10 is a side view of the alignment guide of FIG. 9 and an implant insertion tool showing the alignment guide positioned near the implant insertion tool and in the process of being attached to the implant insertion tool.
Figure 11:
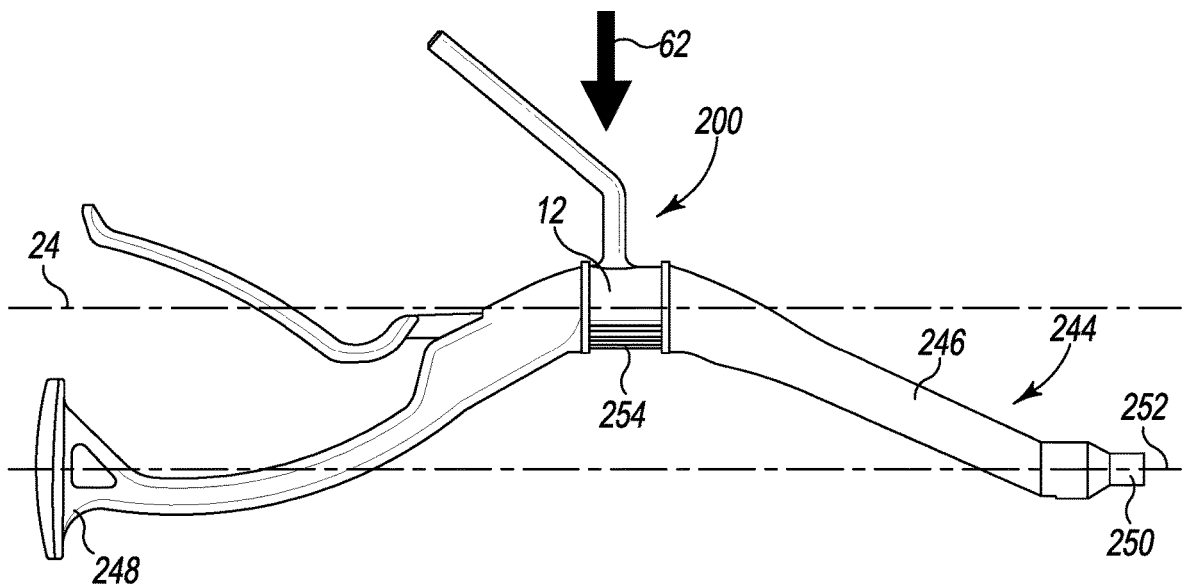
FIG. 11 is a side view of the alignment guide and implant insertion tool of FIGS. 9-10 showing the alignment guide locked on the implant insertion tool.
Figure 12:
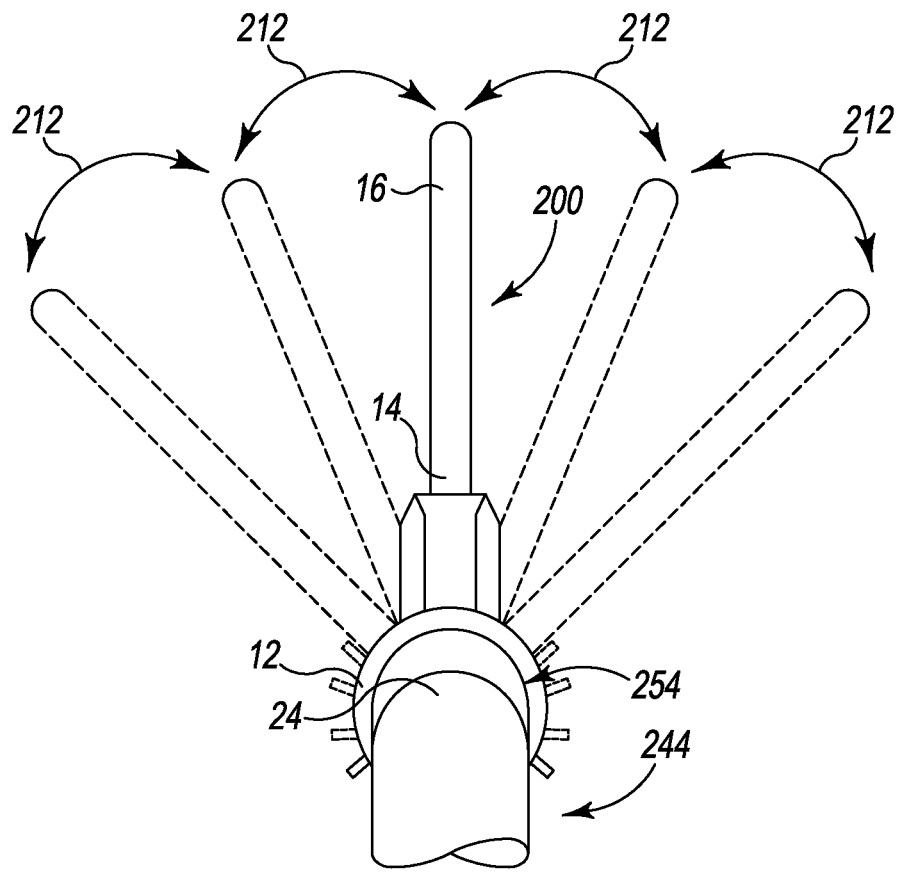
FIG. 12 is a rear view of the alignment guide and implant insertion tool of FIGS. 9-11 showing the alignment guide being rotated about the axis of the implant insertion tool.

Referring now to FIGS. 10-12, in use, the alignment guide 200 may be attached to an implant insertion tool 244. Similar to the insertion tools 44, 144, the illustrative implant insertion tool 244 has an elongated metallic body 246 having an impact head 248 on its proximal end and an attachment mechanism 250 on its distal end. The body 246 defines an imaginary tool axis 252 that extends from the attachment mechanism 250 to the impact head 248. Illustratively, the insertion tool 244 has a curved body 246, which may be used to avoid soft tissue or other patient anatomy. However, in other embodiments the insertion tool 244 may have a straight body 246 similar to the insertion tools of FIGS. 2-5 and 7-8.

The body 246 of the insertion tool 244 includes a mounting surface 254 formed on a section of the body 246. As best shown in FIG. 10, the mounting surface 254 is generally cylindrical. The mounting surface 254 includes multiple ridges or steps 206 running parallel to the tool axis 252. Each pair of ridges 206 is separated by a groove or valley 208.

In use, as shown in FIG. 11, the alignment guide 200 may be coupled, attached or otherwise clipped to the implant insertion tool 244 at the mounting surface 254. To do so, the surgeon or other user places the clip 12 of the alignment guide 200 in contact with the mounting surface 254 and then presses the alignment guide 200 in the downwardly direction 62 toward the implant insertion tool 244. The surgeon may slide the alignment guide 200 onto the implant insertion tool 244 in the direction 62 until the interior surface 26 contacts the implant insertion tool 244. When in contact with the implant insertion tool 244, the teeth 202, 204 engage respective grooves 208 of the mounting surface 254. The teeth 202, 204 and a contact point 210 at the top of the interior surface 26 (shown in FIG. 9) lock the alignment guide 200 to the insertion tool 244 with an interference fit. After contacting the implant insertion tool 244, the axis 24 defined by the alignment guide 200 is parallel to the tool axis 252, as shown in FIG. 11.

In some embodiments, as shown in FIG. 12, the surgeon may rotate the alignment guide 200 about the axis 24 after the alignment guide 200 is attached to the insertion tool 244. As the surgeon rotates the alignment guide 200, the teeth 202, 204 engage respective ridges 206 and grooves 208 in the mounting surface 254. The grooves 208 and ridges 206 cooperate to urge the teeth 202, 204 to come to rest in engagement with respective grooves 208, operating as detents that index rotation of the alignment guide 200. Thus, the alignment guide 200 may be rotated by the surgeon to any of multiple predetermined angles 212 about the axis 24, based on the arrangement of the ridges 206 and grooves 208 of the mounting surface 254. The surgeon may select the angle 212 based on individual preference, to adjust to patient anatomy, or for other reasons. After rotation, the alignment guide 200 remains positively locked to the insertion tool 244 by the teeth 202, 204.

Referring now to FIG. 13, an acetabular cup component being installed in the acetabulum of a patient's hip using an illustrative alignment guide 10 and implant insertion tool 44 is shown. However, it should be understood that the respective alignment guides 100, 200 and insertion tools 144, 244 may also be used in place of the alignment guide 10 and the insertion tool 44. Once the alignment guide 10 and implant insertion tool 44 have been assembled in such a manner as described above, the surgeon secures an acetabular cup component 70 to the insertion tool 44. For example, in some embodiments the acetabular cup component 70 may thread onto a threaded tip of the attachment mechanism 50.

Thereafter, as shown in FIG. 13, the surgeon uses the implant insertion tool 44 to position the acetabular cup component 70 such that its generally hemispherically-shaped bone-engaging surface 72 is inserted into the patient's surgically-prepared acetabular surface 74 in a desired orientation. The surgeon may use the indicator 16 of the alignment guide 10 to measure and adjust the inclination of the acetabular cup component 70. In particular, the surgeon may adjust the angle of the insertion tool 44 until the indicator 16 is parallel with a vertical reference line 76 (i.e., pointing straight up). The vertical reference line 76 may be determined visually by the surgeon in relation to the floor, operating table, or other external reference. Positioning the indicator 16 such that it is parallel with the vertical reference line 76 ensures that the acetabular cup component 70 is positioned with a predetermined inclination angle (based on the particular indication angle 42 of the alignment guide 10 as described above). As shown, the riser 14 positions the indicator 16 away from the tool 44 and thus may improve visibility of the indicator 16, for example by positioning the indicator 16 away from the surgeon's hands, patient anatomy, or other objects that could obscure visibility of the indicator 16.

Once the acetabular cup component 70 is positioned in such a manner, the surgeon strikes the impact head 48 of the implant insertion tool 44 with a surgical mallet, sledge, or other impaction tool to drive the acetabular cup component 70 into the bone tissue until the acetabular cup component 70 is fully seated in the patient's surgically-prepared acetabular surface 74.

The surgeon then releases the acetabular cup component 70 from the implant insertion tool 44. For example, the surgeon may rotate the implant insertion tool 44 in a direction that loosens (i.e., unthreads) the threads of the tool 44 from a corresponding threaded hole of the acetabular cup component 70.

After releasing the acetabular cup component 70, the surgeon removes the alignment guide 10 from the insertion tool 44. The surgeon pulls the alignment guide 10 away from the insertion tool 44 (i.e., opposite the direction 62 of FIG. 3), and the insertion tool 44 passes out of the interior volume 22 through the slot 32. When removing the alignment guide 10, the surgeon may grasp the riser 14 and pull the alignment guide 10 off the insertion tool 44. Additionally or alternatively, if available, the surgeon may pull on one or more of the rounded ledges 102, 104 to assist in removal of the alignment guide 10. Thus, the alignment guide 10 may be removed by the surgeon using one hand.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the apparatus, system, and method described herein. It will be noted that alternative embodiments of the apparatus, system, and method of the present disclosure may not include all of the features described yet still benefit from at least some of the advantages of such features. Those of ordinary skill in the art may readily devise their own implementations of the apparatus, system, and method that incorporate one or more of the features of the present invention and fall within the spirit and scope of the present disclosure.

The invention claimed is:

1. An inclination guide for use with an implant insertion tool during a surgical procedure, the inclination guide comprising a unitary body, the unitary body comprising:
    a clip configured to be coupled to a mounting surface of the implant insertion tool, wherein the clip includes a first curved arm having a first end and a second curved arm having a second end that cooperate to define an interior volume and an imaginary tool axis that extends through the interior volume; and
    an elongated indicator coupled to the clip and extending to a distal end, relative to the clip, at a fixed indication angle defined relative to the imaginary tool axis,
    wherein the first curved arm extends away from the elongated indicator to a first end having a first rounded ledge and the second curved arm extends away from the elongated indicator to a second end having a second rounded ledge, wherein the first and second ends cooperate to define a slot that provides access to the interior volume, and wherein each of the first rounded ledge and the second rounded ledge curves away from the slot.

2. The inclination guide of claim 1, wherein the unitary body comprises a molded polymeric body.

3. The inclination guide of claim 2, wherein the unitary body is formed from polyphenylsulfone (PPSU).

4. The inclination guide of claim 1, wherein the unitary body is formed from a metallic material.

5. The inclination guide of claim 1, further comprising an elongated riser coupled between the clip and the elongated indicator.

6. The inclination guide of claim 5, further comprising a plurality of mounds formed on a surface of the elongated riser.

7. The inclination guide of claim 1, wherein the clip defines a relief opening positioned between the first curved arm and the second curved arm.

8. The inclination guide of claim 1, wherein the first curved arm and the second curved arm define a plano-concave interior surface configured to engage a cylindrical mounting surface of the implant insertion tool.

9. The inclination guide of claim 1, wherein the first curved arm and the second curved arm define a tapered concave interior surface configured to engage a conical frustum mounting surface of the implant insertion tool.

10. The inclination guide of claim 1, wherein the clip comprises an interior surface that confronts the mounting surface of the implant insertion tool while the clip is coupled to the mounting surface, wherein the interior surface includes three contact points, and wherein each of the three contact points is configured to engage the mounting surface of the implant insertion tool.

11. The inclination guide of claim 1, wherein the clip comprises a first tooth and a second tooth that extend inwardly into the interior volume from an interior surface of the clip toward the imaginary tool axis, and wherein the first tooth and the second tooth are configured to engage a respective groove of the mounting surface.

12. The inclination guide of claim 11, wherein the mounting surface comprises a plurality of ridges parallel to the imaginary tool axis, wherein each pair of ridges is separated by a groove.

13. The inclination guide of claim 11, wherein the first tooth is on the first end of the first curved arm, and wherein the second tooth is on the second end of the second curved arm.

* * * * *